(12) United States Patent
Amundsen et al.

(10) Patent No.: US 9,011,608 B2
(45) Date of Patent: Apr. 21, 2015

(54) METHOD AND DEVICE FOR MEASURING DEPOSIT THICKNESS

(75) Inventors: Lene Amundsen, Porsgrunn (NO); Rainer Hoffmann, Skien (NO); Reidar Schüller, Drøbak (NO)

(73) Assignee: Statoil Petroleum AS, Stavanger (NO)

( * ) Notice: Subject to any disclaimer, the term of this patent is extended or adjusted under 35 U.S.C. 154(b) by 756 days.

(21) Appl. No.: 13/147,075

(22) PCT Filed: Jan. 29, 2010

(86) PCT No.: PCT/NO2010/000038
§ 371 (c)(1),
(2), (4) Date: Sep. 2, 2011

(87) PCT Pub. No.: WO2010/087724
PCT Pub. Date: Aug. 5, 2010

(65) Prior Publication Data
US 2011/0308548 A1    Dec. 22, 2011

(30) Foreign Application Priority Data

Jan. 30, 2009  (NO) .................................. 20090491

(51) Int. Cl.
*B08B 9/027* (2006.01)
*G01B 21/08* (2006.01)
(52) U.S. Cl.
CPC ..................................... *G01B 21/085* (2013.01)
(58) Field of Classification Search
CPC ............................... G01B 21/085; B08B 9/027
USPC ............................. 134/1, 5, 8, 19, 22.1, 22.11
See application file for complete search history.

(56) References Cited

U.S. PATENT DOCUMENTS 4,521,864 A * 6/1985 Characklis ................... 702/170
4,843,881 A   7/1989 Hubbard
(Continued)

FOREIGN PATENT DOCUMENTS

| DE | 32 29 609 A1 | 2/1984 |
| EP | 0304708 A2 | 3/1989 |
| RU | 2098756 C1 | 12/1997 |
| SU | 1557454 A1 | 4/1990 |

OTHER PUBLICATIONS

International Search Report, dated Apr. 27, 2010, issued in PCT/NO2010/000038.

(Continued)

*Primary Examiner* — Nicole Blan
*Assistant Examiner* — Natasha Campbell
(74) *Attorney, Agent, or Firm* — Birch, Stewart, Kolasch & Birch, LLP (57) ABSTRACT

The present invention concerns a method for measuring the thickness of any deposit of material on the inner wall of a structure conducting a fluid stream of hydrocarbons, the method comprising the steps of: applying a first heat pulse or continuous heating to at least one first section of the structure removing deposits on the inner wall of the first section of the structure; applying a second heat pulse to both the first section of the structure and at least one second section of the structure, the first and second sections being spaced apart, which heat pulse does not loosen any deposit of material in the second section; measuring the temperature of the wall of the structure or the fluid during the second heat pulse at both the first and second sections; and determining the thickness of any deposit of material on the inner wall of the structure at the second section based on the measured temperatures. The present invention also relates to a corresponding device and arrangement.

13 Claims, 5 Drawing Sheets

(56) References Cited

U.S. PATENT DOCUMENTS

| | | |
|---|---|---|
| 6,886,393 B1 | 5/2005 | Romanet et al. |
| 7,417,009 B2 * | 8/2008 | Shmakova-Lindeman ..... 507/90 |
| 2001/0015213 A1 * | 8/2001 | Clarke .............................. 134/5 |
| 2001/0027684 A1 | 10/2001 | Lotters et al. |
| 2003/0196487 A1 | 10/2003 | Ariyoshi |
| 2004/0059505 A1 * | 3/2004 | Gallagher ........................ 702/1 |

OTHER PUBLICATIONS

Russian Decision on Grant (English translation) for corresponding Russian Application No. 2011135982 dated Jan. 13, 2014.

* cited by examiner

METHOD AND DEVICE FOR MEASURING DEPOSIT THICKNESS

FIELD OF THE INVENTION

The present invention relates to a method of monitoring and measuring the thickness of any deposit of material, especially wax layers and wax build-up from a flow of hydrocarbons, on an inner wall of a structure, such as pipelines and process equipment for oil and gas.

BACKGROUND

Wax deposition at the inside wall of oil pipelines is a severe problem in today's oil production infrastructure. When warm oil flows through a pipeline with cold walls, wax will precipitate and adhere to the walls. This in turn will reduce the pipeline cross-sectional area, which without proper counter measures will lead to a loss of pressure and ultimately to a complete blockage of the pipeline.

Existing technologies that deal with the problem by removing the deposits include:

Pigging: Mechanical scraping off the wax from the pipe wall at regular intervals.

Chemical inhibition: Addition of chemicals which prevent wax deposition.

Direct Electrical Heating (DEH): Electric heating keeps the pipeline warm (above the wax appearance temperature).

Pigging is a complex and expensive operation. If no loop is available, a pig has to be inserted sub-sea using remote-operated vehicles. If more wax is deposited than the pig diameter is designed for the pig might get stuck in the pipeline, resulting in costly operations and stop in production to remove the pig.

Chemical inhibition is also expensive and there are currently no chemicals available that completely reduce wax deposition. The results of such inhibition are uncertain and the intervals and amounts of chemicals used are therefore often unnecessarily high. Further, the chemicals that are used are classified as environmentally very problematic and the dosage of such chemicals should be kept to a minimum.

Electric heating above the wax appearance temperature is very expensive due to both high installation and operational costs. Accordingly, electric heating is not feasible for long-distance transport.

The rate of depositing on the inside surface of a pipeline conducting a multiphase stream of hydrocarbons vary according to several parameters, such as the surrounding temperature (subterranean, air, sea water), the stream temperature, the pressure inside the pipeline, the composition of the stream and the distribution of phases in the stream. Without the possibility to measure the thickness of the deposits in the pipeline or equipment, the remedies above are applied relative often to be on the safe side, in order to avoid problematic build-up of deposits. This results in increased costs and risks in production as well as a negative impact on the environment.

The intervals of the remedies applied are only based on experience data of build-ups in test streams that do not necessarily behave similarly to the actual streams. In addition to the fact that different streams at different production sites behave differently, due to differences in the fluid parameters mentioned above, (temperature, pressure, composition, phase distribution), these parameters will also change in time within one single stream. This may be due to changes of the properties of the produced crude oil and gas which vary in a reservoir depending on degree of exploitation and from reservoir to reservoir. In addition, the profile or shape of the pipeline or any process equipment may have an impact on the rate of deposit build-up, which is not possible to simulate correctly in a laboratory.

In order to know when remediation techniques (e.g. pigging, heating, etc.) have to be applied, it therefore essential to know the current thickness of the wax layer.

Known techniques for determining or measure the current wax layer's thickness include the use of pipeline inspection gauges (pigs), pressure pulse techniques, and pressure drop measurement (over the complete pipeline).

However, each of these known techniques has several drawbacks. For instance, pigs and pressure pulse techniques give no continuous measurement, and they may disturb operation procedures, as well as being expensive. Further, pressure drop measurement only gives an integral measurement over the whole pipe length, not on specific troublesome areas, and the measured pressure drop is influenced by a number of parameters other than wax thickness (e.g. the roughness of the inside of the pipeline), so there is really no direct correlation to wax thickness.

U.S. Pat. No. 6,886,393 describes a method for detecting deposits on the inside of a fluid transporting pipe by the use of a heat source and a sensor, both mounted on a pipe and spaced apart. The heat source provides a thermal gradient and the sensor measures the resulting heat flux which is influenced by the presence of deposits in the pipe as heat is diffused into the fluid when no deposit is present, or transmitted by the pipe when a deposit is present acting as thermal insulation. A threshold for the measured heat flux is used for indicating the presence of deposits. U.S. Pat. No. 6,886,393 also indicates that the thickness of the deposit may be determined by comparing the measured heat flux with a heat flux measured during a calibration stage, however, no details of such calibration is given.

However, the heat flux will be affected by the fluid parameters mentioned above, (temperature, pressure, composition, phase distribution), which constantly change. The method described in U.S. Pat. No. 6,886,393 has no means of calibrating accordingly, taking these parameters into account when a deposit layer is present, and will therefore not provide the necessary accuracy in thickness calculation.

Hence, there is a need for a method for determining the thickness of process side wall deposits in pipelines or production equipment conducting multiphase flow which may perform calibration measurements simultaneously with real-time measurement of deposit thickness.

SUMMARY OF THE INVENTION

It is an object of the present invention to at least partly overcome the above problems, and to provide an improved wax thickness measurement method. This object, and other objects that will be apparent from the following description, is achieved by a method and device according to the appended independent claims. Advantageous embodiments are set forth in the appended dependent claims.

According to a first aspect of the present invention, there is provided a method for measuring the thickness of any deposit of material on the inner wall of a structure conducting a fluid stream of hydrocarbons, the method comprising the steps of:

(a) applying a first heat pulse or continuous heating to at least one first section of the structure removing deposits on the inner wall of the first section of the structure;

(b) applying a second heat pulse to both the first section of the structure and at least one second section of the structure, the first and second sections being spaced apart, which heat pulse does not loosen any deposit of material in the second section;

(c) measuring the temperature of the wall of the structure or the fluid during the second heat pulse at both the first and second sections; and (d) determining the thickness of any deposit of material on the inner wall of the structure at the second section based on the measured temperatures.

The present invention is based on the equations describing transient heat transfer by combined conduction and convection, based on information obtained from an induced transient temperature response. The equations for the heat transfer (for plane parallel geometry) are:

$$HeatFlux = \frac{Q}{A} = U\Delta T = U(T_{Sensor} - T_{Process}) \quad \text{(I)}$$

wherein
Q=heat transfer rate (W)
A=heat transfer surface area (m²)
U=overall heat transfer coefficient (W/(m²·K))
ΔT=difference in temperature
$T_{Sensor}$=temperature at sensor location at outside pipe radius
$T_{Process}$=temperature of process fluid flowing in the pipe In a clean pipe without deposits the overall heat transfer coefficient is:

$$\frac{1}{U} = \frac{\delta_{wall}}{k_{wall}} + \frac{1}{h} \quad \text{(II)}$$

while in a pipe with deposits the equation is:

$$\frac{1}{U} = \frac{\delta_{wall}}{k_{wall}} + \frac{1}{h} + \frac{\delta_{deposit}}{k_{deposit}} \quad \text{(III)}$$

wherein
$\delta_{wall}$=thickness of pipe wall
$k_{wall}$=thermal conductivity of the pipe material (W/mK)
$\delta_{deposit}$=thickness of the deposit
$k_{depositl}$=thermal conductivity of the deposit (W/mK)=
h=internal heat transfer coefficient (W/(m²·K))

It is assumed that the internal heat transfer coefficient h (describing the heat flow from the bulk process fluid to the wall) is the same whether a deposit is present or not. The deposit is considered a part of the wall structure where heat transfer is by conduction only. As the pipe is effectively insulated on the outside, the external heat coefficient is not taken into account.

By measuring the response on a clean section of a pipeline where both the wall thickness of the pipe $\delta_{wall}$, and the thermal conductivity of the pipe material $k_{wall}$ is known, the heat transfer coefficient h, may be calculated by equation (II).

Further, it is assumed that the thermal conductivity $k_{depositl}$ of the deposited material is constant and may be based on laboratory measurements of similar deposits for all practical applications.

The overall heat transfer coefficient, U, may be calculated based on the transient temperature response to a temperature rise caused by a heating element located on the external side of the structure wall according to equation (III). The overall heat transfer coefficient, U, is sensitive to coatings or deposits on the wall, e.g. wax, scale, hydrates, etc.

It is therefore possible to determine the deposit thickness, $\delta_{deposit}$, of any wall layer if the thermal conductivity of the material $k_{deposit}$, is known and the clean structure internal heat transfer coefficient, h, is known.

The internal heat transfer coefficient h, is not affected by the deposit, but is sensitive to the fluid properties and regime of the fluid flowing in the pipe. Hence a constant calibration is necessary in order to take into account the constant change in process fluid composition and phases over time.

The clean structure internal heat transfer coefficient, h, can thus be determined by removing the deposit. Removal is performed by bringing the temperature of the inner wall of the structure above the formation temperature of the deposit, in the case of wax above the wax appearance temperature (WAT), and for hydrates above the hydrate formation temperature.

Hence, in one embodiment of the invention, a heat pulse comprises at least one heating cycle followed by a cooling cycle.

In a further embodiment of the invention the first heat pulse or the continuous heating brings the temperature of the inner wall of the structure of the first section above the appearance temperature of the deposit, in the case of wax above the wax appearance temperature (WAT), and for hydrates above the hydrate formation temperature, such as above about 30° C.

In another embodiment, the second heat pulse brings the temperatures of the inner walls of the structure of the first and second sections above their operating temperatures but at the second section below the appearance temperature of the deposit, in the case of wax below the wax appearance temperature (WAT), and for hydrates below the hydrate formation temperature, such as in the order of about 10° C. above their respective operating temperatures.

Alternatively, the second heat pulse brings about a temperature difference of the inner walls of the structure in both the first and the second section in the order of about 10° C. above their respective operating temperatures.

In another embodiment, the thickness of the deposits on the inner wall at the second section of the structure is determined by correlating the temperatures measured at the first and second sections at a predetermined time after the second heat pulse.

The temperature measurements in step (c) may be performed within the structure wall at a determined distance from the structure outer and/or inner surfaces or on the outer surface of the structure. Alternatively, the temperature measurements in step (c) are performed on the outer surface of the structure.

In a further embodiment the method may comprise additional second sections on the structure for performing steps (b)-(d) for determining deposits thicknesses on the inner wall at other locations of the structure and/or additional first sections on the structure for performing steps (a)-(d) for monitoring the deposit removal functionality of other first sections. Alternatively, the method may comprise predicting the thickness of any deposit of material at one or more portions of the structure remote from second sections by inputting the determined thickness into a material deposition model of the structure.

According to a second aspect of the invention, there is provided a device adapted to perform the above described method. Hence the invention also concerns a device for measuring the thickness of any deposit of material on the inner wall of a structure carrying a hydrocarbon fluid, the device comprising:

at least one first unit, comprising a first sensor means which may be placed (placable) on the structure or in the fluid, for detecting temperatures of structure or fluid, and a first heating means which may be placed (placable) on the outside wall of the structure in proximity of the sensor means for heating the structure, at least one second unit, comprising a second sensor means which may be placed (placable) on the structure or in the fluid, for detecting temperatures of the structure or fluid, and a second heating means which may be placed (placable) on the outside wall of the structure in proximity of the sensor means for heating the structure, wherein said second unit is positioned at a distance from the first unit, and wherein the first unit and second unit are connected to a first means for determining the thickness of any deposit of material on the inner wall of the structure based on the heat flux measured by said first and second units.

In one embodiment of the invention the first and second sensor means of the first and second unit are positioned in the wall of the structure at a determined distance from the structure outer and/or inner surfaces or at the outer surface of the structure, optionally under the corresponding heating means.

In a further embodiment the first and second units may be clamped onto the outer surface of a structure, and alternatively the structure and the first and second units are covered by an insulation layer.

In one embodiment a first device is a central processing means, such as a computer device, which controls the heating and cooling cycles of the first and second device according the method above, while registering the temperatures from the first and second unit, preferably at a predetermined time in the cooling cycle, and even more preferably calculates the thickness of the deposits in the structure based on the recorded temperatures.

In a third aspect, the invention concerns a method and system for removal of deposits on the inner walls of a structure transporting hydrocarbon fluid, when a limit of deposit thickness has been reached, comprising measuring the deposit thickness according the method above, such as at predetermined intervals and automatically initiating removal of the deposits at a predefined thickness value. The method is preferably controlled by an automated control, such as a computer.

The present invention will now be described in further detail by way of example embodiments and with reference to the appended drawings, none of which should be interpreted as limiting of the scope of the invention.

DEFINITIONS

The fluid stream on which the present invention can be applied can be a single phase or multiphase stream comprising hydrocarbons and optionally $H_2O$ and/or gasses such as $CO_2$, $H_2S$ etc. and/or salts and/or additives such as different inhibitors. Advantageously the present invention can be applied to any equipment transporting hydrocarbons.

The equipment may be any type of process equipment that is used to transport hydrocarbons, such as the well itself, the well head, and any pipeline and top-side equipment used in the development or processing of hydrocarbons.

The precipitating material here referred to as "wax" as used within this document refers to solids that precipitate from fluids due to thermodynamically changes. These solids include solids typically dissolved in crude oil at well bore conditions such as asphaltenes, higher paraffins, hydrates, and inorganic and organic salts. The composition of the wax will depend on the origin of the fluid stream.

The "deposit appearance temperature" or "deposit formation temperature" are the same and are meant to be understood as the highest temperature at which a deposit precipitation is observed, for wax the "Wax Appearance Temperature" (WAT) and for hydrates the "Hydrate Appearance Temperature". The exact temperature will depend on the fluid composition and pressure. However, a person skilled in the art can easily obtain this value for instance through simple experimentation.

The "bulk flow temperature" is the temperature of the fluid process stream.

The term "heating means" may comprise any kind of heating device applicable for the specific needs, such as an electric heating element, Direct Electrical Heating (DEH), induced heating or the use of a heat exchanger, such as a water annulus around a section of pipe any equipment part.

The term "heat pulse" is meant to be understood as a change in temperature over a period of time, especially an increase in temperature followed by a decrease in temperature, such as a heat cycle followed by a cooling cycle.

DETAILED DESCRIPTION

The present invention will be described in more detail with reference to the enclosed FIG. 1, which depicts a detailed schematic view of a unit for measuring the thickness of any deposit of material on an inner wall of a structure according to an embodiment of the present invention.

Figure 1:
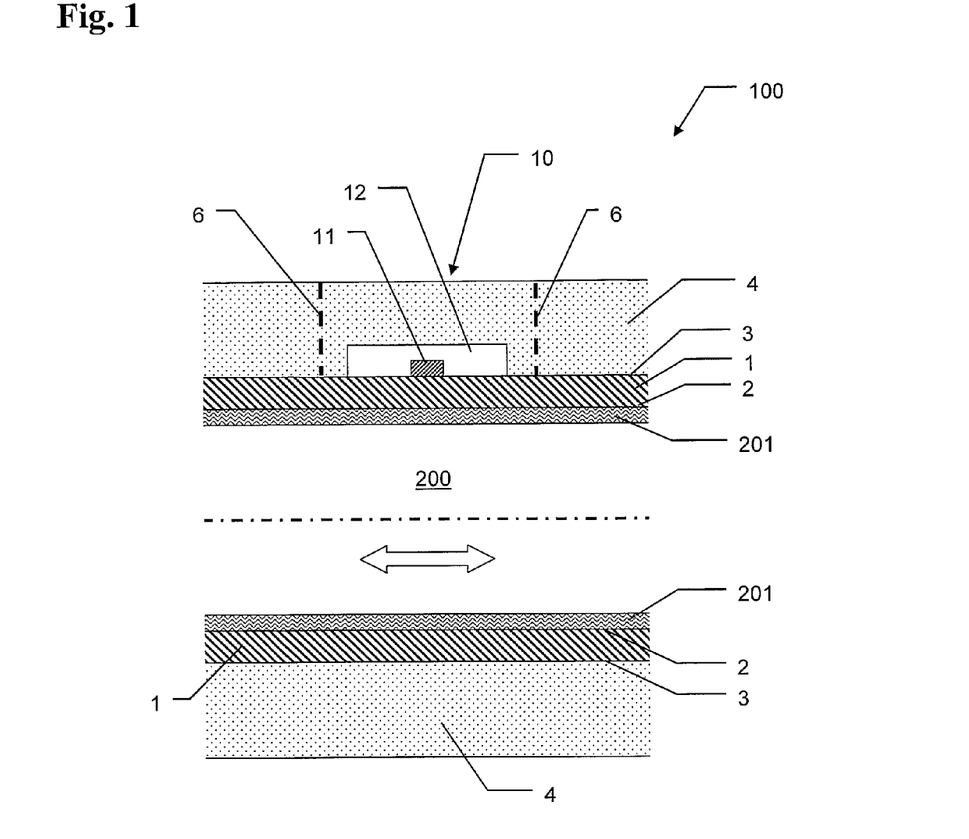
FIG. 1 shows a measuring unit according to an embodiment of the invention.

A measuring unit 10 in FIG. 1 is in this embodiment applied to a pipeline 100 conducting a hydrocarbon fluid stream 200, the pipeline 100 comprising a pipe wall 1, normally made of steel. The pipe wall comprises an inside surface 2 towards the bulk fluid being transported by the pipeline and an outer wall 3, which in this case is covered by an insulation layer 4. A deposit layer 201 is shown present on the inside surface 2 of the pipe wall 1.

The measuring unit 10 may be installed by first removing some of the insulation 4 from a pipeline, such as a steel pipe, such as by incisions 6 cut into the insulation, removing the insulation and attaching the measuring unit 10 onto the pipe and then replacing the cut out insulation on top of the measuring unit, thus also protecting the unit from damage. The measuring unit 10 comprises a heat sensor 11, preferably of point-size, which may be placed directly on the outside surface 3 of the steel wall 1, and a heating means 12 in the form of a heat element covering the heat sensor 11, the heating means 12 preferably being relative flat. The heating means 12 may preferably be wound entirely or partly around the pipe 1. Alternatively the heat sensor 11 and heating means 12 are integrated as one unit for ease of installation.

Figure 2:
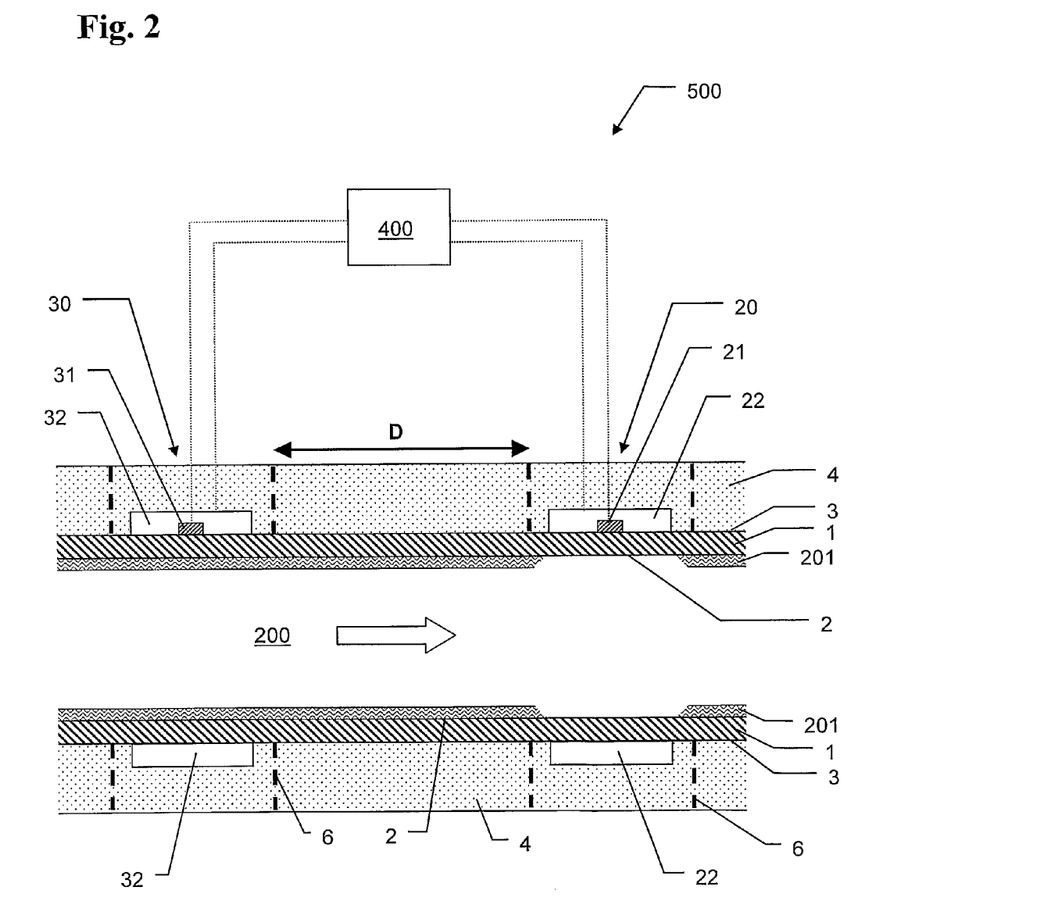
FIG. 2 shows a measuring device according to an embodiment of the invention.

FIG. 2 depicts a measuring device 500 according to the invention comprising a first and a second (measuring) unit, 20 and 30 respectively, placed on first and second sections of the pipeline respectively, and spaced a distance D apart. Both the first 20 and the second 30 unit may be constructed as the above measuring unit 10, comprising a heating zone with heating means in the form of heat elements 22 and 32 and an outlet temperature measurement in the form of a heat sensor device 21 and 31. The temperature measurement is performed on the pipe wall, and both measuring units 20 and 30 may be of the clamp-on type, for ease of installation.

The first unit 20 is in this embodiment positioned downstream from the second unit 30, but the opposite positioning is also possible. Also, the temperature measurements may alternatively be performed directly in the fluid or within the pipe wall at a certain determined distance from the pipe outer and/or inner surfaces, but this would need pre-installation of the units, such as during production of the pipe, or more extensive installation work, the latter being more costly than a "clamp-on solution".

The first unit 20 of the measuring device 500 according to the invention is used for reference/calibration measurement of the multiphase flow at a pipe section without deposit, preferably in real-time.

The first measuring unit 20 therefore either operates intermittently of the wax thickness measurements by applying a preparatory high temperature heat pulse in a cleaning cycle, or at a constant high temperature for constant cleaning, both embodiments providing enough heat to remove any wax or hydrate deposit on the internal wall 2 of its pipe section. This is indicated in FIG. 2 where no deposit material 201 is present on the inside wall 2 of a first pipe section covered by the first heating means 22 of the first measuring unit 20. It should also be noted that both heating devices of the two sections in FIG. 2 surround the pipeline 1, indicated by each heating means being present on both the top and bottom parts of the pipeline 1, whereas in FIG. 1, the heating means 12 only partly surrounds the pipeline 1. Depending on the amount of heat supplied by the first heating means 22, the deposit material directly under the corresponding heat sensor 21 must at least be removed, preferably also the deposits directly under the heating means 22, and alternatively also adjacent deposits to some extent. If any inner surface areas of the pipe adjacent to the area directly under the heating means are cleaned by the first heating means, the corresponding heat sensor might alternatively be positioned to any side of the heating means underneath which the inner wall surface of the pipe is clean. This might e.g. be the situation at the immediate downstream area of the heating means.

High temperature in this context means a temperature above the deposit appearance temperature; above the wax appearance temperature (WAT) for waxes and above the hydrate formation temperature for hydrates.

It has been discovered that it is possible to loosen already deposited wax from a pipe wall by quickly increasing the wall temperature above the WAT as a limited pulse which does not dissolve the wax but only loosens it, thus enabling transport of the wax as particles. The wax is ripped off the wall by the fluid process stream as solid particles and can be transported downstream and have no or very low tendency to be deposited on the walls or other surfaces of the structure.

The wax in the first section may thus be loosened either as solid parts by such a limited heat pulse or by melting the wax by a longer heat pulse from the heating device 22 to clean the section before a measuring cycle. Alternatively continuous heating by the heating device 22 may keep the first section clean at all times. Melting the wax re-dissolves the wax into the flow, transporting it downstream where it may deposit again on the pipe wall, or any other surface of equipment handling the stream, which is undesirable. Especially, such re-deposition may occur at vulnerable positions, where local build-up of wax may appear. Therefore, keeping the pipe wall at operation temperature, allowing deposits to build, and then provide a short heat pulse for removing the deposits as particles before a measuring cycle, may be preferable.

The cleaning cycle is important to obtain a reference/calibration value for the heat transfer coefficients since the heat transfer coefficients of multiphase flow are not known a priori. Hence, during this cleaning cycle the first unit 20 may measure the heat transfer from the pipe wall (the steel) to the multiphase flow.

After the cleaning cycle, or during the continuous cleaning, the inside wall 2 of the pipe section of the first unit 20 is clean and free of all deposits and ready for use as reference/calibration during the measuring cycle of the wax thickness, at the position of the second unit 30. The inner wall surface 2 of the pipeline beneath the first unit 20 is considered to remain clean for the purpose of the measuring cycle, as deposit build-up is insignificant in the short duration of the measuring cycle. In principle, the first measuring unit 20 is therefore considered to measure on a clean pipe section.

To perform the measuring cycle for measurement of the wax thickness, both the first 20 and second 30 unit run the same heating/cooling cycle of the heating elements 22 and 32 and for both units the temperature change during the heating/cooling cycle is recorded by the heat sensors 21 and 31 respectively and are preferably relayed to a first device 400, which preferably is a control and recording unit, such as a computer. The actuation of the cleaning and heating cycles is also preferably controlled by said first device.

The first 20 and second 30 units may be identical for ease of production and delivery, as well as installation, but the heating power of at least the first unit has to be important enough so as to not only provide a measurement pulse but also provide a cleaning pulse for removing deposits as mentioned above.

By generating a short and constant power input from the heating elements 22 and 32, the temperature sensors 21 and 31 respectively, below said elements, will register a temperature rise versus time as shown in the chart according to FIG. 3. As soon as the heating elements are switched off, the temperature of the pipe wall will decrease, as registered by the first and second sensors 21 and 31.

Figure 3:
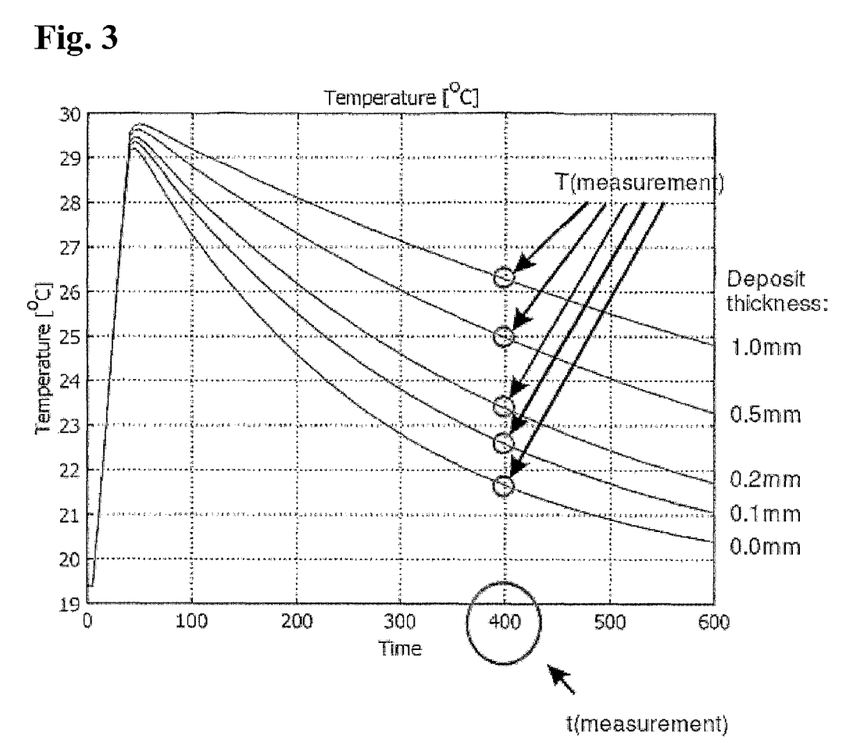
FIG. 3 is an exemplary x-y chart, showing Time vs. Pipeline Wall Temperatures.

FIG. 3 shows a an x-y chart, wherein the Pipeline Wall Temperatures is plotted against time. At about time zero the pipe wall is for example at an operating temperature, such as about 19.5° C., without any heat supplied by the heating elements. A measuring cycle is initiated by the constant power output of the heating elements which is applied in a predetermined period, as seen by the steady temperature increase measured by the heat sensors. This rise in temperature of the outer pipeline wall 3 is practically identical both with or without deposit.

At a maximum allowed applied temperature, or in this case at a predetermined time, the power of the heating elements are switched off, and the temperature drop in the pipe wall is registered. The results in FIG. 3 show clearly that the speed at which the temperature drops is a function of deposit layer thickness. The wall deposit 201 acts as an insulating layer which reduces the wall heat flux and slows down the cooling rate of the pipe wall. The thicker the deposit, the longer time it takes for the pipe wall to cool down in the second section. The bottom temperature curve in the chart of FIG. 3 will corresponds to the measurement of the first measuring unit 20 which measures the temperature development on a clean inner pipe wall.

It should be noted that the maximum applied temperature is relatively low, in this case below 30° C., such as about 29.5°

C., as the heat pulse generated during the measuring cycle must not bring the inner wall temperature of the second pipe section above appearance temperature of the deposit, which for wax may be about 30° C. If the temperature of the second pipe section is brought above this limit, or if the heating is applied too long, the wax and/or hydrate deposit may loosen and be ripped off the inner pipe wall by the fluid flow, and the measurement of the deposit thickness would be compromised as the thickness beneath the second unit would not correspond to the overall deposit thickness in the pipeline/equipment, but be less important, which might cause misinterpretation of when to effectuate deposit removal measures. Hence, in such a case, deposit removal measures might be caused to be effected at a too late stage and the wax thickness cause problems in operations, due to a low reading which does not represent the actual wax level.

In the case of a continuous heating at the first section, the first heating element 22 is provided with an additional power during the measuring cycle equal to the power supplied to the second section, by the second heating means 32. Hence, in such an embodiment, the first temperature sensor 21 registers the temperature curve from a different base line temperature, such as at a temperature above 30° C., and the registered temperatures are corrected and correlates to the registrations of the second sensor. If for example, the normal wall temperature without heating is 20° C. and the measurement heat pulse at the second section rises to 30° C. during the heat pulse, then the first reference sensor 21 of the first unit 20, could operate permanently at 50° C. (i.e. above WAT) with the first heating means 22 providing a heat pulse up to 60° C. A requirement would be that the material properties are not temperature dependent.

The device according to the present in invention is in a preferable embodiment non-intrusive, and may be of a clamp-on type, which makes it quick and easy to install on both existing and new equipment, and even to move to different locations or to replace in case of damage or malfunction. The device may also be integrated in pipes and equipment, preferably during production of such parts.

EXAMPLE 1

Figure 4:
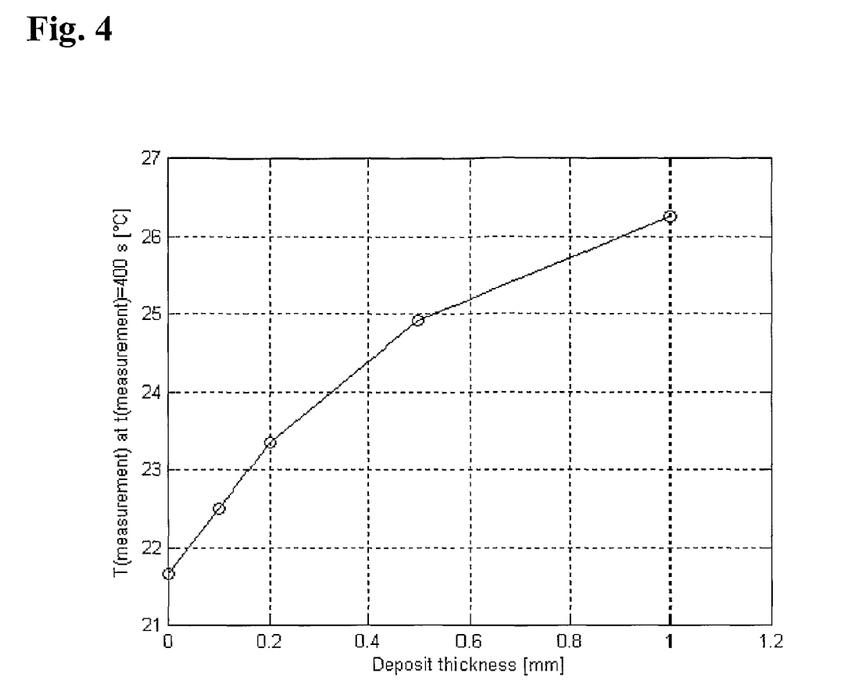
FIG. 4 is an exemplary x-y chart, showing Deposit Thickness vs. Pipeline Wall Temperatures.

The following example shows a method for conducting a measurement with various deposit thicknesses, with reference to FIG. 3 and FIG. 4:

After a cleaning cycle at the first unit 20, comprising activation of the first heating element 22, heating the inside wall 2 of a pipeline above the wax appearance temperature, and cooling of the pipe wall 1 in the first section to the same temperature as that of the second section, the heat elements 22 and 23 are switched on from t=10 s to t=40 s with a constant electric power of 400 W.

This heating generates a linear rise of the measured temperature at the position of the heat sensors as seen in FIG. 3. When the heat elements are switched off, the generated heat will dissipate. Due to the insulating effect of the deposit this will take longer with growing deposit thickness. A certain measurement time t(measurement) is defined, preferably at a time where the spread between the temperature curves for minimum and maximum deposit thickness is largest, in order to obtain the best resolution and accuracy of the measurements. The minimum deposit curve, i.e. the lower curve in FIG. 3, will be the curve of the first temperature sensor 21, (and also the second sensor 31 in case no deposits are present, which result would translate to a clean pipe). The maximum deposit curve will be that of the second temperature sensor 31 and the position and profile of the curve will depend on the deposit thickness.

In this example the largest spread between the minimum curve and the maximum curves occurs at t=400 s. At this time a measurement the value T (measurement) is registered and correlated to the deposit thickness. The temperatures at the chosen time after the heating element is switched off is used for calculation of the wall layer thickness as shown in FIG. 4.

The chart in FIG. 4 shows the curve of the calculated deposit thickness with the measured temperature values of T (measurement), taken at the time t (measurement), in this example at t=400. For the example shown here, a deposit thickness of only 0.1 mm generates a temperature difference of almost 1° C., shown as the second plot value from the left on the curve, a temperature difference which is unproblematic to detect with currently available temperature sensors. Hence, the method may provide measurements of high accuracy, especially in relation to the large diameters of oil pipelines which may for example be in the order of 10 to 1400 cm, and normally between 50 to 120 cm.

EXAMPLE 2

Figure 5:
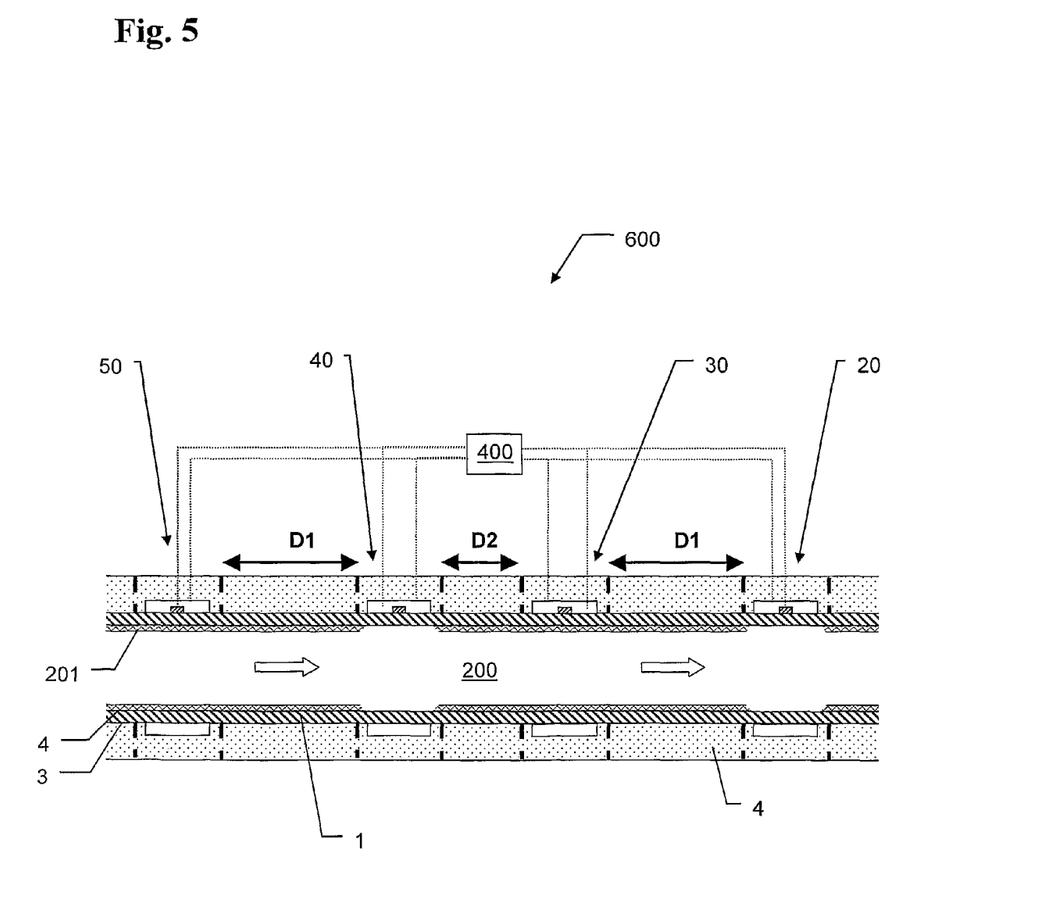
FIG. 5 shows an alternative measuring device according to an embodiment of the invention.

In alternative arrangement of the present invention as illustrated in FIG. 5, several measurement units 20, 30, 40 and 50 of the type described above are arranged at different locations along the pipeline. Further, a central processing means 400 (e.g. a computer device) is provided, which central processing means is adapted to receive local wax layer thickness data from all the measurement devices.

By including additional units of the second type 30 such as device 50, local deposit thicknesses may be measured at different location, based on a central calibration of one unit of the first type 20. By including additional units of the first type 20 such as unit 40, the reference data and calibration of other first type units, such as unit 20 may be monitored and controlled against malfunction, which might have serious effects. In addition, such additional first type units could alternatively also be used as second type units after a cleaning of the pipeline, if desired. First and second units may be identical in constructions and operation, and may used interchangeably.

The received local data may be also be used by the processing means 400 to predict the wax layer thickness at location remote from where the measurement units are located, using a wax deposition model of the pipeline, as well as to update the present wax deposition model of the pipeline.

Certainly, the arrangement of FIG. 5 could also be used without the wax deposition model. In such a case, the output is a plurality of point measurements, one at the position of each pair of measurement units making up separate measurement devices, such as the pair of units 20 and 30 and the pair of units 40 and 50, each pair of units at least comprising a unit for both cleaning and measuring cycle, and one unit for measuring cycle. This arrangement would be especially applicable when measuring at locations of different material properties and types of structures, such as different types of pipelines with different thickness, material etc, or different types of equipment connected to the pipeline or each other.

CONCLUSION

The solutions to the transient system are mathematically well defined, and it is possible to perform calculations that give the temperature response for a given deposit thickness (e.g. FIG. 3). It is also possible to do the calculations in the reverse order; from a transient temperature response it is possible to calculate the deposit thickness.

The invention makes use of the heat insulating properties of a deposit to measure its thickness by the analysis of a transient response. A transient analysis results in a significantly higher accuracy than a steady-state analysis. A reference probe (such as the first measuring unit 20) is used to eliminate the influence of multi-phase flow behaviour on heat transfer ensuring applicability for all types of multi-phase flow regimes.

The method provides non-invasive, relatively cheap, accurate and frequently usable measurement of wax deposit build-up. Further the method is non-intrusive by use of a "clamp-on" design and may be attached to the pipe after construction without disturbing operation.

Wax deposit build-up can be measured without any equipment in the main flow and thus maintain a clear pig path for deposit removal when necessary. Further, measurements may be performed frequently, e.g. daily, thus providing clear control of wax thickness growth, and indicating the right moment for counter-actions.

The system according to the present invention is cost-efficient if the same process equipment, such as a water annulus present for wax removal, can be re-used for the measurement purpose.

As noted in example 2, the system may be operated with spatial dependency for longer pipe segments by measuring temperatures at intermediate points.

The person skilled in the art will realize that the present invention by no means is limited to the preferred embodiment(s) described above. On the contrary, many modifications and variations are possible within the scope of the appended claims.

For instance, the present invention is applicable to all kinds of structures or containers that handle hydrocarbon streams comprising components that possibly deposit on the container wall, e.g. wax, scale, hydrates etc.

The invention claimed is:

1. A method for measuring the thickness of any deposit of material on the inner wall of a structure conducting a fluid stream of hydrocarbons, the method comprising the steps of:
   (a) applying a first heat pulse or continuous heating to at least one first section of the structure removing deposits on the inner wall of the first section of the structure;
   (b) applying a second heat pulse to both the first section of the structure and at least one second section of the structure, the first and second sections being spaced apart, which heat pulse does not loosen any deposit of material in the second section;
   (c) measuring the temperature of the wall of the structure or the fluid during the second heat pulse at both the first and second sections; and
   (d) determining the thickness of any deposit of material on the inner wall of the structure at the second section based on the measured temperatures.

2. A method according to claim 1, wherein the first or second heat pulse comprises at least one heating cycle followed by a cooling cycle.

3. A method according to claim 1, wherein the first heat pulse or the continuous heating brings the temperature of the inner wall of the structure of the first section above the appearance temperature of the deposit, in the case of wax above the wax appearance temperature (WAT), and for hydrates above the hydrate formation temperature.

4. A method according to claim 1, wherein the second heat pulse brings the temperatures of the inner walls of the structure of the first and second sections above their operating temperatures but at the second section below the appearance temperature of the deposit, in the case of wax below the wax appearance temperature (WAT), and for hydrates below the hydrate formation temperature.

5. A method according to claim 3, wherein the appearance temperature of the deposit is about 30° C.

6. A method according to claim 1, wherein the second heat pulse brings about a temperature difference of the inner walls of the structure in both the first and the second section in the order of about 10° C. above their respective operating temperatures.

7. A method according to claim 1, wherein the thickness of the deposits on the inner wall at the second section of the structure is determined by correlating the temperatures measured at the first and second sections at a predetermined time after the second heat pulse.

8. A method according to claim 1, wherein the temperature measurements in step (c) are performed within the structure wall at a determined distance from the structure outer and/or inner surfaces.

9. A method according to claim 1, wherein the temperature measurements in step (c) are performed on the outer surface of the structure.

10. A method according to claim 1, further comprising additional second sections on the structure for performing steps (b)-(d) for determining deposits thicknesses on the inner wall at other locations of the structure.

11. A method according to claim 1, further comprising additional first sections on the structure for performing steps (a)-(d) for monitoring the deposit removal functionality of other first sections.

12. A method according to claim 10, further comprising predicting the thickness of any deposit of material at one or more portions of the structure remote from second sections by inputting the determined thickness into a material deposition model of the structure.

13. A method for removal of deposits on the inner walls of a structure transporting hydrocarbon fluid, comprising measuring the deposit thickness according to claim 1, at predetermined intervals and automatically initiating removal of the deposits at a predefined thickness value.

* * * * *